United States Patent
Ketola et al.

(10) Patent No.: US 9,840,523 B2
(45) Date of Patent: Dec. 12, 2017

(54) PROCESS OF SYNTHESIZING DIISOPROPYLAMINO-DISILANES

(71) Applicant: Dow Corning Corporation, Midland, MI (US)

(72) Inventors: Barry M. Ketola, Freeland, MI (US); Brian D. Rekken, Midland, MI (US); Xiaobing Zhou, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/300,987

(22) PCT Filed: May 29, 2015

(86) PCT No.: PCT/US2015/033092
§ 371 (c)(1),
(2) Date: Sep. 30, 2016

(87) PCT Pub. No.: WO2015/184214
PCT Pub. Date: Dec. 3, 2015

(65) Prior Publication Data
US 2017/0029446 A1    Feb. 2, 2017

Related U.S. Application Data

(60) Provisional application No. 62/004,917, filed on May 30, 2014.

(51) Int. Cl.
*C07F 7/02* (2006.01)
*C07F 7/10* (2006.01)
*C07F 7/12* (2006.01)

(52) U.S. Cl.
CPC ............ *C07F 7/10* (2013.01); *C07F 7/12* (2013.01); *C07F 7/126* (2013.01)

(58) Field of Classification Search
CPC ............ C07F 7/10; C07F 7/12; C07F 7/126

USPC ........................................... 556/410
See application file for complete search history.

(56) References Cited

U.S. PATENT DOCUMENTS

| 7,019,159 | B2 | 3/2006 | Dussarrat et al. |
| 7,064,083 | B2 | 6/2006 | Dussarrat et al. |
| 7,875,312 | B2 | 1/2011 | Thridandam et al. |
| 8,043,907 | B2 | 10/2011 | Ma et al. |
| 8,367,854 | B2 | 2/2013 | Knies et al. |
| 8,927,400 | B2 | 1/2015 | Foad et al. |
| 9,221,787 | B2 | 12/2015 | Zahler et al. |
| 9,337,018 | B2 | 5/2016 | Xiao et al. |
| 2012/0277457 | A1 | 11/2012 | Lehmann et al. |
| 2013/0319290 | A1 | 12/2013 | Xiao et al. |
| 2013/0323435 | A1 | 12/2013 | Xiao et al. |
| 2015/0024608 | A1 | 1/2015 | Mayorga et al. |
| 2016/0203975 | A1 | 7/2016 | Xiao et al. |

OTHER PUBLICATIONS

Schuh et al., Z. anorg. allg. Chem. 619 (1993) 1347-1352.*
Schuh, H.; Schlosser, T.; Bissinger, P.; Schmidbaur, H., "Disilanyl-Amines—Compounds Comprising the Structrual Unit Si—Si—N, As Single-Source Precursors for Plasma-Enhanced Chemical Vapour Deposition (PE-CVD) of Silicon Nitride", Z. Anorg. Allg. Chem. (1993), 619, 1347-1352.
H.J. Frenck et al., Application and Possibilities of the Remote PECVD Process to Deposition of Thin Nitride Films from Metalorganic Sources, ISPC-10 Bochun, Aug. 1991, 2.4-28, pp. 1-6.

* cited by examiner

*Primary Examiner* — Sudhakar Katakam
*Assistant Examiner* — Kofi Adzamli
(74) *Attorney, Agent, or Firm* — Matthew T. Fewkes

(57) ABSTRACT

Chemical processes comprise selectively synthesizing diisopropylamino-disilanes and reduction of chloride in aminosilanes, and the compositions comprise the diisopropylamino-disilanes and at least one reaction by-product prepared thereby. The diisopropylamino-disilanes are diisopropylamino-pentachlorodisilane and diisopropylamino-disilane.

7 Claims, No Drawings

PROCESS OF SYNTHESIZING DIISOPROPYLAMINO-DISILANES

CROSS REFERENCE TO RELATED APPLICATIONS

This application is a U.S. national stage filing under 35 U.S.C. §371 of PCT Application No. PCT/US15/033092 filed on 29 May 2015, currently pending, which claims the benefit of U.S. Provisional Patent Application No. 62/004,917 filed 30 May 2014 under 35 U.S.C. §119 (e). PCT Application No. PCT/US15/033092 and U.S. Provisional Patent Application No. 62/004,917 are hereby incorporated by reference.

The field of this invention generally relates to chemical processes and compositions prepared thereby. The chemical processes comprise selectively synthesizing diisopropylamino-disilanes, and the compositions comprise the diisopropylamino-disilanes and at least one reaction by-product prepared thereby. The processes further comprise reducing chloride impurities in aminosilanes, including aminodisilanes.

Aminosilanes, chlorosilanes, and aminochlorosilanes may be used to prepare silicon-based materials such as silicon-based lubricants, elastomers, and resins.

In U.S. Pat. No. 8,043,907 B2, Y. Ma, et al. report a method of fabricating a non-volatile memory device on a substrate. Silicon precursors may be used to form materials of poly-silicon, silicon oxide, silicon oxynitride, silicon nitride, and hafnium-containing materials. The silicon precursor may be a silane, alkylsilanes, halosilane, alkoxysilane, am inosilane, aminodisilane, silylazide, silylhydrazine, or derivative thereof. Examples of the silicon precursor are, among others, hexachlorodisilane and 1,1,2,2-tetrachlorobis(diisopropylamino) disilane. There is little correlation of the particular silicon precursor to the type of material it may be used to form.

H. J. Frenck, et al. report using bis(diisopropylamino) disilane to deposit a silicon nitride film (*Application and Possibilities of the Remote PECVD Process to Deposition of Thin Nitride Films From Metalorganic Sources*, ISPC-10 Bochun, August 1991, 2.4-28, pages 1-6).

Aminochlorodisilanes and am inodisilanes have been difficult to synthesize in good yield and at commercial scale. We believe the synthetic difficulties include their high reactivity and molecular instability, which may lead to side reactions, decomposition, isomerization, or a combination thereof with starting materials and/or reaction products. We think a process having improved selectivity for the synthesis of these compounds over decomposition and/or isomerization by-products would enable the making of compositions comprising higher yields and/or concentrations of the synthesized disilanes and/or lower concentrations of reaction by-product(s). Furthermore, the production of aminosilanes with reduced chloride impurities has been difficult. We believe a process to reduce chloride impurities would offer improved performance in chemical deposition applications.

BRIEF SUMMARY OF THE INVENTION

We have discovered improved processes for synthesizing diisopropylamino-disilanes. The processes have higher yield and/or selectivity than comparative processes. Embodiments of the invention include:

A process of synthesizing diisopropylamino-pentachlorodisilane, which is of formula (A):$[(CH_3)_2CH]_2NSiCl_2SiCl_3$ (A), the process comprising: contacting, in a hydrocarbon vehicle, hexachlorodisilane ($SiCl_3SiCl_3$) with a source of diisopropylamino group to give a higher yield of the compound of formula (A) compared to the yield, if any, of a compound of formula (B): $[(CH_3)_2CH]_2NSiCl_2SiCl_2N[CH(CH_3)_2]_2$ (B); wherein the source of diisopropylamino group is, relative to the hexachlorodisilane, from 0.50 to 1.19 molar equivalents of a metal diisopropylamide, $[(i-Pr)_2N]_m M^A$, wherein i-Pr is isopropyl and subscript m is 1 or 2, wherein when m is 1, $M^A$ is an element of Group I of the Periodic Table of the Elements and when m is 2, $M^A$ is an element of Group II of the Periodic Table of the Elements, or the source of diisopropylamino group is from 1.0 to 2.39 molar equivalents of diisopropylamine, or the source of diisopropylamino group is a mixture of from 0.50 to 1.19 molar equivalents of diisopropylamine ($(i-Pr)_2NH$) and from 0.50 to 1.19 molar equivalents of pyridine or a trialkylamine ($Alkyl_3N$), wherein each alkyl independently is a ($C_2$-$C_{10}$) alkyl.

A process of synthesizing diisopropylamino-disilane, which is of formula (I): $[(CH_3)_2CH]_2NSiH_2SiH_3$ (I), the process comprising: contacting, in a solvent characterizable by a boiling point, a metal aluminum hydride with diisopropylamino-pentachlorodisilane to give diisopropylamino-disilane characterizable by a boiling point, wherein the boiling point of the solvent is at least 90 degrees Celsius (° C.) and is at least 10° C. higher than the boiling point of diisopropylamino-disilane; and separating the diisopropylamino-disilane from the solvent to give a purified form of the diisopropylamino-disilane in at least 30% yield and a purity greater than or equal to 70 area percent by gas chromatography (70 area % (GC)).

A composition comprising the diisopropylamino-substituted disilane compound synthesized by any one of the processes and at least one reaction by-product of that process. Each reaction by-product is different than the compound synthesized by the respective process. The diisopropylamino-substituted disilane compound synthesized by the respective process is the compound of formula (A) or (I), respectively.

The compound of formula (A) is useful in making the compound of formula (I) according to the process of synthesizing diisopropylamino-disilane. The compound of formula (I), and the respective composition comprising same and respective reaction by-product(s), independently are useful as silicon yielding precursors for making silicon-containing materials for electronic and photovoltaic devices. The compounds of formulas (A) and (I), and the respective compositions comprising same and respective reaction by-product(s), have additional uses not related to electronic or photovoltaic semiconductor applications, e.g., for making silicon-based lubricants, elastomers, and resins. The invention process may have additional uses unrelated to these applications.

We have also discovered a process for reducing chloride impurities in aminosilanes, including disilanes. The process provides aminosilanes having lower levels of chloride impurities than other processes. Embodiments of the invention include:

A process for reducing chloride levels in aminosilanes, the process comprising:

combining i) a metal hydride or ii) a metal amide salt to an aminosilane composition comprising the aminosilane and a chloride species to produce a mixture of the aminosilane and a reaction product formed by the reaction of the metal hydride or the metal amide salt and the chloride species; and distilling the mixture to recover the aminosilane.

DETAILED DESCRIPTION OF THE INVENTION

The Brief Summary and Abstract are incorporated here by reference. The invention embodiments, uses and advantages summarized above are further described below.

The invention has technical and non-technical advantages. One of the problems solved by the processes is providing, relative to comparative processes, improved processes of making the diisopropylamino-substituted disilane compounds of formulas (A) and (I). For instance, the process of synthesizing the compound of formula (A) improves upon a first comparative process that disadvantageously uses 3.0 molar equivalents of diisopropylamine (as reactant and acid scavenger) in the contacting step instead of the present source of diisopropylamino group. The process of synthesizing the compound of formula (I) improves upon a second comparative process that disadvantageously uses monoglyme (i.e., $CH_3OCH_2CH_2OCH_3$) as vehicle in the contacting step instead of the present solvent. Improvements over other comparative processes are contemplated too.

Depending upon the particular aspect of the process of synthesizing the compound of formula (A) being used, the process independently produces said compound of formula (A) in higher purity, higher yield, greater selectivity, or a combination of any two or more thereof, than the first comparative process. For example, the first comparative process produces a mixture of the compounds of formulas (A) and (B), which after purifying the mixture gives the compound of formula (A) in 7% yield and the compound of formula (B) in 43% yield. In favorable contrast, the present process gives the compound of formula (A) in 30% yield, preferably after purification thereof to a purity of 90 area % (GC). Therefore, the present process synthesizes the compound of formula (A) with increased selectivity for (A) over (B), and in higher yield of (A).

Certain aspects of the process of synthesizing the compound of formula (A) use the metal diisopropylamide, $[(i-Pr)_2N]_m M^4$, alternatively a mixture of the metal diisopropylamide and diisopropylamine, as the source of the diisopropylamine. The process using metal diisopropylamide helpfully produces a metal chloride as a reaction by-product rather than an alkylammonium chloride such as diisopropylammonium chloride (i.e., diisopropylamine hydrochloride) or trimethylammonium chloride (i.e., triethylamine hydrochloride). The compound of formula (A) is advantageously easier to separate from the metal chloride reaction by-product than from the alkylammonium chloride reaction by-product. For example, the metal chloride may be filtered off and away from the compound of formula (A) more easily than filtering off diisopropylamine hydrochloride.

Further, certain aspects of the process of synthesizing the compound of formula (A) may avoid or minimize production of an undesired decomposition by-product, diisopropylaminotrichlorosilane, compared to the first comparative process.

Depending upon the particular aspect of the process of synthesizing the compound of formula (I) being used, the process advantageously produces said compound of formula (I) in higher purity, higher yield, greater selectivity, or a combination of any two or more thereof, than the second comparative process. For example, the boiling point of the solvent independently is beneficially at least 90° C. and is at least 10° C. higher than the boiling point of the diisopropylamino-disilane. This difference in boiling points enhances purification of the compound of formula (I). In contrast the second comparative process produces a reaction mixture containing monoglyme, and it is more difficult to separate the compound of formula (I) from monoglyme (b.p. 85° C.) using an evaporative technique (e.g., distillation), especially on industrial scale, than it is to separate the compound of formula (I) from the solvent using the same technique. This advantage may be due to the effective difference in boiling points between the compound of formula (I) and the solvent versus the less effective difference between the said compound and monoglyme in the second comparative process. The greater the present difference in boiling points, the more effective the evaporative technique of the present process becomes.

Further, in the process of synthesizing the compound of formula (I), even though the boiling point of the solvent independently is at least 90° C. and is at least 10° C. higher than the boiling point of the diisopropylamino-disilane, the freezing point of the reaction mixture formed in the contacting step may be low enough to advantageously provide a wide range of temperatures for operating the process, such as from −60° C. to 100° C., alternatively −40° C. to 100° C., alternatively −30° C. to 100° C. The operating temperature of the reaction mixture may be greater than the freezing point thereof and less than or equal to the boiling point of the lowest boiling component thereof (where the component is in sufficient quantity to affect vapor pressure thereof). In some aspects the freezing point of the reaction mixture is the freezing point (f.p.) of the solvent in the reaction mixture, which f.p. may be less than or equal to the melting point of the solvent. Generally, the lower the melting point, the lower the freezing point. The solvent may function to dissolve at least some of the metal aluminum hydride at such temperature, and as the reduction of the compound of formula (A) to the compound of formula (I) proceeds, additional metal aluminum hydride may dissolve in the solvent, and become more available for reaction. Also, the boiling point of the solvent is significantly higher than the boiling point of monoglyme, thereby enabling the present process of synthesizing the compound of formula (I) to be conducted at higher reaction mixture temperatures. The higher temperatures may increase manufacturing plant productivity for a given plant capacity. Thus, the solvent improves options for running the reaction and purifying the compound of formula (I) on an industrial scale compared to the second comparative process using monoglyme.

Further, it may turn out that the yield of the compound of formula (I) may be higher and/or the amount(s) of any Si-containing reaction by-product(s) may be lower, using the solvent compared to the comparative yields of said compounds using the monoglyme.

The process of synthesizing the compound of formula (I) generates metal aluminum chloride as a solid reaction by-product. The process employs the solvent, which may beneficially support or enable formation of a stable slurry of the metal aluminum chloride in the solvent. Advantageously, the compound of formula (I) may be distilled directly from the stable slurry. Thus, the process enables purification of the compound of formula (I) from the reaction mixture without the need to filter off the metal aluminum chloride solid and/or evaporate the solvent before the distillation.

Another advantage is certain aspects of the process of synthesizing the compound of formula (I) may produce a reaction mixture lacking a compound of formula (II): $[(CH_3)_2CH]_2NSiH_2SiH_2N[CH(CH_3)_2]_2$ (II), which may be a by-product of over reaction that is formed during the contacting step. Another advantage is certain aspects of the process of synthesizing the compound of formula (I) may produce a mixture of the compound of formula (I) and a compound of formula (II): $[(CH_3)_2CH]_2NSiH_2SiH_2N[CH(CH_3)_2]_2$ (II), wherein the relative amounts thereof may be adjusted by varying the process.

Another advantage is certain aspects of the process of reducing chloride impurities in the aminosilane, including aminodisilanes, may produce aminosilanes with reduced chloride contents compared to known processes and these reduced-chloride aminiosilanes are believed to perform better in chemical deposition processes.

The invention and advantages are not limited to solutions of the aforementioned problems or to the above advantages. Certain aspects of this invention may independently solve additional problems and/or have other advantages.

Aspects of the invention are described herein using various common conventions. For example, all states of matter are determined at 25° C. and 101.3 kPa unless indicated otherwise. All % are by weight unless otherwise noted or indicated. All % values are, unless otherwise noted, based on total amount of all ingredients used to synthesize or make the composition, which adds up to 100%. Any Markush group comprising a genus and subgenus therein includes the subgenus in the genus, e.g., in "R is hydrocarbyl or alkenyl," R may be alkenyl, alternatively R may be hydrocarbyl, which includes, among other subgenuses, alkenyl. For U.S. practice, all U.S. patent application publications and patents referenced herein, or a portion thereof if only the portion is referenced, are hereby incorporated herein by reference to the extent that incorporated subject matter does not conflict with the present description, which would control in any such conflict.

Aspects of the invention are described herein using various patent terms. For example, "alternatively" indicates a different and distinct embodiment. "Comparative" as used in comparative example, comparative process or comparative method means a non-invention experiment and should not be interpreted as prior art. "Comprises" and its variants (comprising, comprised of) are open ended. "Consists of" and its variants (consisting of) are closed ended. "Contacting" means bringing into physical contact. "May" confers a choice, not an imperative. "Optionally" means is absent, alternatively is present.

Aspects of the invention are described herein using various chemical terms. The meanings of said terms correspond to their definitions promulgated by IUPAC unless otherwise defined herein. For convenience, certain chemical terms are defined herein.

The term "ether" means an aprotic compound that is an alkylene glycol dialkyl ether or a monofunctional dialkyl ether. The term "alkylene glycol dialkyl ether" means a compound of formula (G): $R^4O—((C_2-C_{10})\text{alkyleneO})_m—R^4$ (G), wherein m is an integer from 1 to 20 and each $R^4$ independently is a $(C_1-C_{10})$alkyl with the proviso that the compound of formula (G) has a total of at least 6 carbon atoms. Each of the $(C_1-C_{10})$alkyl and $(C_2-C_{10})$alkylene independently is straight chain or, when having 3 or more carbon atoms, branched chain. The $(C_2-C_{10})$alkylene may be straight chain of formula $—(CH_2)_g—$, wherein g is an integer from 2 to 10. When m is 1, the alkylene glycol dialkyl ether may be called a simple alkylene glycol dialkyl ether. When m is 2 to 20, the alkylene glycol dialkyl ether may be called a polyalkylene glycol dialkyl ether. The term "monofunctional dialkyl ether" means a compound of formula (S): $R^4OR^4$ (S), wherein each $R^4$ independently is a $(C_1-C_{10})$alkyl with the proviso that the compound of formula (S) has a total of at least 6 carbon atoms. Each of the $(C_1-C_{10})$alkyl and $(C_2-C_{10})$alkylene independently is straight chain or, when having 3 or more carbon atoms, branched chain.

The term "composition" means chemical matter that may be defined by an empirical formula of its constituent elements.

"Compounds" having different structures may differ from each other in at least one property, function, and/or use.

The term "halogen" means fluorine, chlorine, bromine or iodine, unless otherwise defined.

The term "IUPAC" refers to the International Union of Pure and Applied Chemistry.

The term "lack" means free of or a complete absence of.

The term "metal aluminum hydride" means an agent of formula $M^B[Al(H/D)_4]_b$, the agent comprising at least one aluminum-hydrogen or aluminum-deuterium functional group, wherein H is hydrogen; D is deuterium; "H/D" independently is H, D, or a combination of H and D (e.g., 3 H and 1 D, 2 H and 2 D, or 1 H and 3 D); b is 1 or 2; and $M^B$ is a metal that is not aluminum; wherein when b is 1, $M^B$ is an element of Group I; and wherein b is 2, $M^B$ is an element of Group II of the Period Table of the Elements. The agent is useful for reducing halosilanes to hydridosilanes.

"Periodic Table of the Elements" means the version published 2011 by IUPAC.

The term "purify" means to increase concentration of a desired ingredient (up to ≤100%, alternatively up to <100%); or to decrease concentration of one or more undesired ingredients (down to ≥0%, alternatively down to 0%, alternatively down to >0%), whether or not concentration of the desired ingredient has been increased; or both.

The term "reaction by-product" means a secondary product of a chemical transformation of one or more reactants.

The term "remainder" means a portion that is left behind, e.g., a pot residue after a distillation or a filtercake after a filtration.

The term "rod" means a material restricted in two dimensions, e.g., having an aspect ratio >2.

The term "separate" means to cause to physically move apart, and thus as a result is no longer in direct touching.

The term "substrate" means a physical support having at least one surface upon which another material may be hosted.

The term "vehicle" means a material acting as a carrier, hosting medium, or solvent for another material, which may or may not be soluble therein. The vehicle may be a liquid.

An inventive aspect is the process of synthesizing diisopropylamino-pentachlorodisilane, which is of formula (A): $[(CH_3)_2CH]_2NSiCl_2SiCl_3$ (A). The process comprises contacting, in a hydrocarbon vehicle, hexachlorodisilane $(SiCl_3SiCl_3)$ with a source of diisopropylamino group to give a higher yield of the compound of formula (A) compared to the yield, if any, of a compound of formula (B): $[(CH_3)_2CH]_2NSiCl_2SiCl_2N[CH(CH_3)_2]_2$ (B), wherein i-Pr is isopropyl.

The composition and the amounts of the source of diisopropylamino group is conceived to enable said higher yield of the diisopropylamino-pentachlorodisilane. The source of diisopropylamino group may be, relative to the hexachlorodisilane, from 0.50 to 1.19 molar equivalents of a metal diisopropylamide, $[(i-Pr)_2N]_mM^A$, wherein subscript m is 1 or 2, wherein when m is 1, $M^A$ is an element of Group I of the Periodic Table of the Elements and when m is 2, $M^A$ is an element of Group II of the Periodic Table of the Elements. Alternatively, the source of diisopropylamino group may be, relative to the hexachlorodisilane, from 1.0 to 2.39 molar equivalents of diisopropylamine. Alternatively, the source of diisopropylamino group may be, relative to the hexachlorodisilane, a mixture of from 0.50 to 1.19 molar equivalents of diisopropylamine ((i-Pr)$_2$NH) and from 0.50 to 1.19 molar equivalents of pyridine or a trialkylamine (Alkyl$_3$N), wherein each alkyl independently a (C$_2$-C$_{10}$)alkyl. The amount of pyridine or a trialkylamine may be from 0.90 to 1.10 times the molar amount of diisopropylamine in the mixture. The amount of pyridine or a trialkylamine may be equimolar (i.e., 1.00 times the molar amount) with the amount of diisopropylamine in the mixture. The yield of the compound of formula (A) is greater than or equal to 30%, alternatively >50%, alternatively >70%.

The composition and the amounts of the source of the diisopropylamino group relative to the hexachlorodisilane are conceived to give the diisopropylamino-pentachlorodisilane in an yield greater than the yield of any compound of formula (B): [(CH$_3$)$_2$CH]$_2$NSiCl$_2$SiCl$_2$N[CH(CH$_3$)$_2$]$_2$ (B). For example when the source of the diisopropylamino group is the metal diisopropylamide, as the molar equivalents of the metal diisopropylamide is increased from 0.50 to 1.00, the theoretical yield of the diisopropylamino-pentachlorodisilane is increased from 50% to 100%. Also, as the molar equivalents of the metal diisopropylamide is increased from 0.50 to 1.19, the actual yield of the diisopropylamino-pentachlorodisilane may be increased from 30% to ≤100%. Similarly when the source of the diisopropylamino group is the diisopropylamine, as the molar equivalents of the diisopropylamine is increased from 1.00 to 2.00, the theoretical yield of the diisopropylamino-pentachlorodisilane is increased from 50% to 100%. As the molar equivalents of the diisopropylamine is increased from 1.00 to 2.39, the actual yield of the diisopropylamino-pentachlorodisilane may be increased from 30% to ≤100%. Similarly when the source of the diisopropylamino group is the mixture of diisopropylamine and pyridine or a trialkylamine, as the molar equivalents of each of the diisopropylamine and pyridine or a trialkylamine are increased from 0.50 to 1.00, the theoretical yield of the diisopropylamino-pentachlorodisilane is increased from 50% to 100%. As the molar equivalents of each of the diisopropylamine and pyridine or a trialkylamine are increased from 0.50 to 1.19, the actual yield of the diisopropylamino-pentachlorodisilane may be increased from 30% to ≤100%.

In some aspects of the process of synthesizing the compound of formula (A), the metal diisopropylamide, [(i-Pr)$_2$N]$_m$M$^4$, is used as the source of the diisopropylamino group in the contacting step. When m is 1, M$^4$ is Li, Na, K, Rb, Cs, or Fr; alternatively Li, Na, K, Rb, or Cs; alternatively Li, Na, K, or Cs; alternatively Li, Na, or K; alternatively Li or Na; alternatively Li or K; alternatively Na or K; alternatively Li; alternatively Na; alternatively K. When m is 2, M$^4$ is Be, Mg, Ca, Sr, Ba, or Ra; alternatively Mg, Ca, or Ba; alternatively Mg or Ca; alternatively Mg or Ba; alternatively Ca or Ba; alternatively Mg; alternatively Ca. In some aspects m is 1 and M$^4$ is Li, Na, or K; or m is 2 and M$^4$ is Mg or Ca. In some aspects the metal diisopropylamide is used as the source of the diisopropylamino group in the contacting step and m is 1 and M$^4$ is lithium, sodium, or potassium; or m is 2 and M$^4$ is magnesium or calcium. The molar equivalent of the metal diisopropylamide may be from 0.8 to 1.15, alternatively from 0.90 to 1.11, all relative to the hexachlorodisilane. The yield of the compound of formula (A) is greater than or equal to 30%, alternatively >50%, alternatively >70%.

In other aspects of the process of synthesizing the compound of formula (A), the mixture of the diisopropylamine and pyridine or a trialkylamine is used as the source of the diisopropylamino group in the contacting step. The molar equivalents of the diisopropylamine is from 0.8 to 1.15, alternatively from 0.90 to 1.11 and the molar equivalents of the pyridine or a trialkylamine is from 0.8 to 1.15, alternatively from 0.90 to 1.11, both relative to the hexachlorodisilane. The yield of the compound of formula (A) is greater than or equal to 30%, alternatively >50%, alternatively >70%.

In other aspects of the process of synthesizing the compound of formula (A), the diisopropylamine ((i-Pr)$_2$NH) is used as the source of the diisopropylamino group in the contacting step. The molar equivalents of diisopropylamine is from 1.0 to 2.39, alternatively from 1.5 to 2.29, alternatively from 1.90 to 2.15. The yield of the compound of formula (A) is greater than or equal to 30%, alternatively >50%, alternatively >70%.

In the process of synthesizing the compound of formula (A) the contacting step independently may be operated at any temperature that enables the process of synthesizing the compound of formula (A). The contacting may be operated at a temperature of from −30° C. to 50° C., alternatively from −20° C. to 45° C., alternatively from −10° C. to 40° C. The operating temperature of the reaction mixture may be greater than the freezing point thereof and less than or equal to the boiling point of the lowest boiling component thereof (where the component is in sufficient quantity to affect vapor pressure thereof). The contacting may be continued for any period of time sufficient to give the compound of formula (A). The contacting independently may be continued for a period of time sufficient to give the diisopropylamino-pentachlorodisilane in a yield greater than 30%.

In the process of synthesizing the compound of formula (A) the contacting step, in the hydrocarbon vehicle, of the hexachlorodisilane (SiCl$_3$SiCl$_3$) with the source of diisopropylamino group is conducted by adding the source of the diisopropylamino group to the hexachlorodisilane.

The process of synthesizing the compound of formula (A) produces a reaction by-product. For example, depending on the particular aspect of the process of synthesizing the compound of formula (A), when the source of the diisopropylamino group is diisopropylamine, the process produces a by-product that is diisopropylamine hydrochloride. When the source of the diisopropylamino group is the mixture of diisopropylamine and pyridine or a trialkylamine the process produces a by-product that is pyridine hydrochloride or trialkylamine hydrochloride. When the source of the diisopropylamino group is the metal diisopropylamide, the process produces a by-product that is a metal chloride, wherein the metal is M$^4$ as described above. The process may further comprise separating the diisopropylamino-pentachlorodisilane from the solid reaction by-product to give a solution comprising the diisopropylamino-pentachlorodisilane in the hydrocarbon vehicle, the solution being free of the solid by-product. The solid by-product may be separated by any suitable method such as filtration or centrifugation followed by decantation.

The process of synthesizing the compound of formula (A) may further comprise one or more optional steps before the contacting step or one or more optional steps after the contacting step, or both. For example, before the contacting step the processes may further comprise a step of synthesizing the hexachlorodisilane and/or synthesizing the metal diisopropylamide. Also, in the process of synthesizing the compound of formula (A), the process may further comprise a step mixing diisopropylamine and pyridine or a trialkylamine to prepare the mixture of the diisopropylamine and pyridine or a trialkylamine.

Alternatively or additionally, after the contacting step, the process of synthesizing the compound of formula (A) may further comprise separating the hydrocarbon vehicle from the diisopropylamino-pentachlorodisilane to give a concentrated form of the diisopropylamino-pentachlorodisilane. The process may further comprise separating the diisopropylamino-pentachlorodisilane from any other components of the respective concentrated form to give a purified form of the diisopropylamino-pentachlorodisilane. For example, the process may further comprise distilling the diisopropylamino-pentachlorodisilane from the concentrated form thereof to give a purified form of the diisopropylamino-pentachlorodisilane. The diisopropylamino-pentachlorodisilane of the purified form thereof may be obtained in at least 50% yield (based on the amount of hexachlorodisilane used in the contacting step) and a purity greater than or equal to 80%, alternatively 90%, alternatively 93%, wherein the maximum purity may be 100%, alternatively 99.9999999%, alternatively 99.999999%, alternatively 99.99999%, alternatively 99.9999%, alternatively 99.999%, alternatively 99.99%, alternatively 99.9%, alternatively 99.0%, all % being area % (GC). The high purities of the compound of formula (A) may improve purity of the compound of formula (I) synthesized therefrom in the other process.

The process of synthesizing the compound of formula (A) is carried out in a hydrocarbon vehicle. The hydrocarbon vehicle may comprise an alkane having at least 5 carbon atoms, a cycloalkane having at least 5 carbon atoms, an arene having at least 6 carbon atoms, or a mixture of any two or more thereof. The hydrocarbon vehicle may comprise a pentane, hexane, hexanes, cyclohexane, a heptane, benzene, toluene, a xylene, or a mixture of any two or more thereof. The hydrocarbon vehicle may be any one of the same used in the Examples described later.

The composition of the hydrocarbon vehicle may be conceived to optimize the contacting steps (e.g., selecting a hydrocarbon vehicle having a boiling point for achieving a desired reaction temperature or a hydrocarbon vehicle lacking ability to solubilize a reaction by-product). Additionally or alternatively, the composition of the hydrocarbon vehicle may be conceived to optimize the optional separating step (e.g., selecting a hydrocarbon vehicle having a desired boiling point enabling evaporation thereof without evaporating the compound of formula (A)). The hydrocarbon vehicle may consist of carbon and hydrogen atoms or may be a halogenated hydrocarbon vehicle consisting of carbon, hydrogen, and halogen atoms. The hydrocarbon vehicle consisting of C and H atoms may be alkanes, aromatic hydrocarbons, and mixtures of any two or more thereof. The alkanes may be hexanes, cyclohexane, heptanes, isoparaffins, or mixtures of any two or more thereof. The aromatic hydrocarbon may be toluene, xylenes, or mixtures of any two or more thereof. The halogenated hydrocarbon vehicle may be dichloromethane. The hydrocarbon vehicle may remain in the reaction mixture when the reduction contacting step is performed; alternatively the hydrocarbon vehicle may be removed from the reaction mixture prior to performing the reduction contacting step. The process having different compositions for hydrocarbon vehicle may differ from each other in at least one result, property, function, and/or use. Different compositions of the hydrocarbon vehicle may provide different solubilities for the compound of formula (A), the source of the diisopropylamino group, a reaction by-product, or a combination of any two or more thereof.

In some aspects of synthesizing the compound of formula (A), the source of the diisopropylamino group is the mixture of diisopropylamine and pyridine or a trialkylamine ($Alkyl_3N$). The mixture may comprise diisopropylamine and pyridine; alternatively diisopropyl amine and a trialkylamine, wherein each alkyl independently a ($C_2$-$C_{10}$)alkyl; alternatively diisopropylamine, pyridine, and at least one trialkylamine. Each ($C_2$-$C_{10}$)alkyl of the trialkylamine may be the same, alternatively at least two ($C_2$-$C_{10}$)alkyl, alternatively all three ($C_2$-$C_{10}$)alkyl may be different. The ($C_2$-$C_{10}$)alkyl may be straight chain or branched. The ($C_2$-$C_{10}$)alkyl may be ethyl, propyl, isopropyl, butyl, isobutyl, sec-butyl, tertiary butyl, a pentyl, a hexyl, a heptyl, an octyl, a nonyl, or a decyl. Examples of the trialkylamine are triethylamine, diisopropylethylamine, dim ethyl-tert-butylamine, tripropylamine, tributylamine, and a mixture of any two or more thereof. The trialkylamine may be triethylamine, tripropylamine, or tributylamine; alternatively triethylamine; alternatively tripropylamine; alternatively tributylamine.

Another inventive aspect is a process of synthesizing diisopropylamino-disilane, which is of formula (I): $[(CH_3)_2CH]_2NSiH_2SiH_3$ (I), the process comprising: Contacting, in a solvent characterizable by a boiling point, a metal aluminum hydride with diisopropylamino-pentachlorodisilane to give diisopropylamino-disilane characterizable by a boiling point; and Separating the diisopropylamino-disilane from the solvent to give a purified form of the diisopropylamino-disilane in at least 30% yield and a purity greater than or equal to 70 area % (GC). The boiling point of the solvent is at least 90° C. and is at least 10° C. higher than the boiling point of diisopropylamino-disilane.

In some aspects of the process of synthesizing the compound of formula (I), the composition, boiling point of the solvent, and optionally freezing point of the reaction mixture, are conceived to give the purified form of the diisopropylamino-disilane in at least 30% yield and a purity greater than or equal to 70 area % (GC). For example, the solvent, alternatively an ether, may consist of carbon, hydrogen and oxygen atoms or may be a halogenated solvent, alternatively ether, consisting of carbon, hydrogen, oxygen, and halogen atoms. In one embodiment, the solvent is an ether, alternatively alkylene glycol dialkyl ether. The alkylene glycol dialkyl ether may be the compound of formula (G). The alkylene glycol dialkyl ether may be a tetraethylene glycol di($C_1$-$C_4$)alkyl ether, propylene glycol di($C_4$-$C_8$)alkyl ether, ethylene glycol di($C_4$ or $C_8$)alkyl ether, or a combination of any two or more thereof. E.g., the alkylene glycol dialkyl ether may be tetraethylene glycol dimethyl ether, propylene glycol dioctyl ether, or ethylene glycol dioctyl ether. The halogenated alkylene glycol dialkyl ether may be a tetraethylene glycol halo-substituted di($C_1$-$C_4$)alkyl ether, propylene glycol halo-substituted di($C_2$-$C_4$)alkyl ether, ethylene glycol halo-substituted di($C_3$ or $C_4$)alkyl ether, or a combination of any two or more thereof. E.g., the halogenated alkylene glycol dialkyl ether may be tetraethylene glycol bis(trifluoromethyl) ether, propylene glycol bis(3,3,3-trifluoropropyl) ether, or ethylene glycol bis(3,3,3-trifluorobutyl) ether. The ether may be a monofunctional dialkyl ether. The monofunctional dialkyl ether may be the compound of formula (S). The monofunctional dialkyl ether may be a symmetrical compound or unsymmetrical compound. The symmetrical compound may be dipropyl ether, dibutyl ether, dipentyl ether, dihexyl ether, diheptyl ether, dioctyl ether, dinonyl ether, or didecyl ether. The unsymmetrical compound may be propyl butyl ether, octyl propyl ether. The ether may be a mixture of two or more alkylene glycol dialkyl ethers, alternatively a mixture of two or more monofunctional dialkyl ethers, alternatively a mixture of at least one alkylene glycol dialkyl ether and at least one monofunctional dialkyl ether. The ether may be removed from the reaction mixture after completion of the reduction contacting step, alternatively the ether may be left in a remainder and the compound of formula (I) may be removed (e.g., distilled) from the remainder to separate it from the ether. The process using different compositions for the ether may differ from each other in at least one result, property, function, and/or use. In some aspects the ether is the alkylene glycol dialkyl ether and the alkylene glycol dialkyl ether is a tetraethylene glycol di($C_1$-$C_4$)alkyl ether, propylene glycol di($C_4$-$C_8$)alkyl ether, ethylene glycol di($C_4$ or $C_8$)alkyl ether, or a combination of any two or more thereof. Alternatively, the alkylene glycol dialkyl ether is tetraethylene glycol dimethyl ether, propylene glycol dipropyl ether, ethylene glycol dibutyl ether, pentaethylene glycol dimethyl ether, hexaethylene glycol dimethyl ether, or a polyethylene glycol dimethyl ether. Alternatively, the alkylene glycol dialkyl ether is selected from a group consisting of any five of the following members: tetraethylene glycol dimethyl ether, propylene glycol dipropyl ether, ethylene glycol dibutyl ether, pentaethylene glycol dimethyl ether, hexaethylene glycol dimethyl ether, and a polyethylene glycol dimethyl ether. Alternatively, the alkylene glycol dialkyl ether is tetraethylene glycol dimethyl ether, alternatively propylene glycol dipropyl ether, alternatively ethylene glycol dibutyl ether, alternatively pentaethylene glycol dimethyl ether, alternatively hexaethylene glycol dimethyl ether, alternatively a polyethylene glycol dimethyl ether. Different compositions of the ether may provide different solubilities for the compound of formula (A), the compound of formula (I), the metal aluminum hydride, a reaction by-product, or a combination of any two or more thereof.

In some aspects of the process of synthesizing the compound of formula (I), the boiling point of the solvent is at least 30° C. higher, alternatively at least 50° C. higher than the boiling point of diisopropylamino-disilane. The boiling point of the solvent may be as high as 275° C., alternatively 225° C., alternatively 200° C. In some aspects the contacting is performed at a temperature of from −60° C. to 100° C., alternatively from −20° C. to 100° C., alternatively from −20° C. to 60° C. provided that the temperature is greater than the freezing point of the reaction mixture formed in the contacting step. The reaction mixture may freeze by solidification of the solvent therefrom. The melting point of the alkylene glycol dialkyl ether may be as low as −30° C. The melting point of the monofunctional dialkyl ether may be as low as −122° C. (dipropyl ether).

In some aspects of the process of synthesizing the compound of formula (I), the contacting step is continued for a period of time sufficient to give the diisopropylaminodisilane in greater than 30% yield.

In some aspects the process of synthesizing the compound of formula (I) may be enhanced by configuring purity of starting materials and/or the synthesized compound of formula (I) and/or configuring the technique of the process steps. Such enhancements may produce the yield of the purified form of the diisopropylamino-disilane being at least 60% and/or wherein the purified form of the diisopropylamino-disilane is free of any 1,2-bis(diisopropylamino)-disilane. The diisopropylamino-disilane may be purified under vacuum such as via fractional distillation in vacuo through a distillation column. Alternatively, the diisopropylamino-disilane may be purified via a technique other than distillation, even a non-evaporative technique.

In some aspects of the process of synthesizing the compound of formula (I), the process may further comprise combining i) a metal hydride or ii) a metal amide salt with the diisopropylaminodisilane synthesized.

The metal hydride may be any metal hydride comprising a metal from group I or Group II of the Periodic Table of the elements, alternatively the metal hydride comprises lithium or aluminum. In one embodiment, the metal hydride is lithium tris-(tert-butoxy)-aluminum hydride, lithium triethylborohydride, or sodium triethylborohydride. Metal hydrides are available commercially from, for example, Sigma Aldrich.

The metal amide may be an amide comprising any metal from group I or Group II of the Periodic Table of the Elements, alternatively, the metal of the metal amide is lithium. In one embodiment the metal amide is lithium diisopropylamide. Metal amides are available commercially from, for example, Sigma Aldrich.

The metal amide and/or metal hydride may be added alone (neat) or as a solution or slurry, depending upon solubility, in a solvent such as toluene, tetrahydrofuran, cyclohexane, or tetraethylene glyclol dimethylether.

The amount of metal amide and/or metal hydride combined with the am inosilane and/or aminodisilane is from equal molar amount to an excess molar amount compared to the amount of chloride impurities in the aminosilane or aminodisilane, alternatively the molar ratio of metal amide and/or metal hydride to the chloride impurity is >1, alternatively at least 2, alternatively from >1 to 100.

The temperature of that the metal hydride or metal amide are combined is typically from −20° C. to 110° C., alternatively from −20 to 20° C. One skilled in the art could determine the optimum temperature to combine the metal hydride or metal amide.

The metal hydride and/or metal amide are combined with the am inosilane and/or aminodisilane for at least 1 minute, alternatively for at least 15 minutes, alternatively from 15 minutes to 24 hours.

The order of addition of the combining of the am inosilane and/or aminodisilane with the metal hydride and/or metal amide is not critical.

In some aspects of the process of synthesizing the compound of formula (I) the separating step may comprise distilling the diisopropylamino-disilane from the solvent, and optionally from any solid reaction by-products, to give a distillate that is the purified form of the diisopropylaminodisilane. Alternatively, the separating may comprise a non-distillation method of evaporating the diisopropylaminodisilane from the solvent to give a condensate that is the purified form of the diisopropylamino-disilane.

In some aspects of synthesizing the compound of formula (I), the process comprises: contacting, in a solvent, characterizable by a boiling point, a metal aluminum hydride with bis(diisopropylamino)-pentachlorodisilane to give diisopropylamino-disilane characterizable by a boiling point that is at least 10° C. higher than the boiling point of the solvent; adding a second solvent characterizable by a boiling point that is at least 10° C. higher than the boiling point of the diisopropylamino-disilane; separating the solvent from the diisopropylamino-disilane and the second solvent; and then separating the diisopropylamino-disilane from the second solvent to give a purified form of the diisopropylaminodisilane in at least 30% yield and purity of at least 70 area % (GC).

Alternatively or additionally in the process of synthesizing the compound of formula (I), the diisopropylaminodisilane of the purified form thereof may be obtained in a purity greater than or equal to 80%, alternatively 90%, alternatively 93%, wherein the maximum purity may be 100%, alternatively 99.9999999%, alternatively 99.999999%, alternatively 99.99999%, alternatively 99.9999%, alternatively 99.999%, alternatively 99.99%, alternatively 99.9%, alternatively 99.0%, all % being area % (GC). The high purities of the compound of formula (I) synthesized by the process may enable greater stability and longer shelf-life thereof.

Alternatively or additionally in the process of synthesizing the compound of formula (I), the diisopropylpentachloro-disilane used in the contacting steps may be synthesized according to any one of the aspects of the process of synthesizing the compound of formula (A). In some aspects the compounds of formulas (A) and (I) may be made sequentially in the same reactor.

In some aspects the process of synthesizing the compound of formula (I) may be enhanced by configuring relative amounts of reactants of the process steps. In some aspects of the process of synthesizing the compound of formula (I) the relative amounts of the diisopropylamino-pentachlorodisilane and metal aluminum hydride are characterizable by a molar ratio of Si—Cl groups of the diisopropylamino-pentachlorodisilane to H atoms (and/or D atoms) of the metal aluminum hydride from 1.0:0.5 to 1.0:1.5, alternatively 1.0:0.8 to 1.0:1.5, alternatively from 1.0:1.0 to 1.0 to 1.5.

In some aspects the process of synthesizing the compound of formula (I) may be further defined by the nature of the metal aluminum hydride. The metal of the metal aluminum hydride is not aluminum. The metal aluminum hydride may be a Group I or Group II metal aluminum hydride. The Group II metal aluminum hydride may be of formula $M^B(AlH_4)_2$ or $M^B(AlD_4)_2$, alternatively $M^B(AlH_4)_2$, alternatively $M^B(AlD_4)_2$, wherein $M^B$ is the Group II metal and each H is a hydrogen atom, and D is a deuterium atom. Examples of the Group II metal aluminum hydride are magnesium aluminum hydride and calcium aluminum hydride. Alternatively the metal aluminum hydride may be the Group I metal aluminum hydride. The Group I metal aluminum hydride may be of formula $M^B AlH_4$ or $M^B AlD_4$, alternatively $M^B AlH_4$, alternatively $M^B AlD_4$, wherein $M^B$ is the Group I metal, H is a hydrogen atom, and D is a deuterium atom. The Group I metal, $M^B$, may be Li, Na, or K. Examples of the Group I metal aluminum hydride are $KAlH_4$, $NaAlH_4$, $LiAlH_4$, $KAlD_4$, $NaAlD_4$, and $LiAlD_4$. The Group I metal aluminum hydride may be $KAlH_4$, $NaAlH_4$, or $LiAlH_4$; alternatively $NaAlH_4$ or $LiAlH_4$; alternatively $KAlH_4$; alternatively $NaAlH_4$; alternatively $LiAlH_4$; alternatively $KAlD_4$, $NaAlD_4$, or $LiAlD_4$; alternatively $NaAlD_4$ or $LiAlD_4$; alternatively $KAlD_4$; alternatively $NaAlD_4$; alternatively $LiAlD_4$. Alternatively, the metal aluminum hydride may be a combination of any two or more of the aforementioned examples. E.g., the metal aluminum hydride may be a combination of $NaAlH_4$ and $LiAlH_4$ or a combination of $LiAlH_4$ and $Mg(AlH_4)_2$. Typically at least some, alternatively all, of the metal aluminum hydride is $LiAlH_4$.

The processes having different compositions for metal aluminum hydride may differ from each other in at least one result, property, function, and/or use. Different metal aluminum hydrides may provide different reducing activity and/or selectivity.

In some embodiments, the metal aluminum hydride does not further comprise a complexing agent. In other embodiments the metal aluminum hydride further comprises a complexing agent, which would form a dative bond to Al.

The complexing agent may be an aprotic compound containing O, N or S, such as an alkyl ether (e.g., diethyl ether), oxacycloalkane (e.g., tetrahydrofuran), or a trialkylamine (e.g., trimethylamine). The complexing agent may be used to enhance shelf stability, modulate reactivity, or the like, of the metal aluminum hydride. The complexing agent may be removed from the reaction mixture prior to performing the reduction contacting step.

Metal aluminum hydrides suitable for use in the process are generally known. Suitable metal aluminum hydrides may be readily obtained from a commercial supplier such as Sigma-Aldrich Company (St. Louis, Mo., USA) and/or prepared by any suitable process. In some embodiments, the metal aluminum hydride does not further comprise a trialkylaluminum. In other embodiments the metal aluminum hydride further comprises a trialkylaluminum.

The orders of addition in the contacting steps may be important. For example, in the process of synthesizing the compound of formula (A) the source of diisopropylamino group is added to a mixture of the hexachlorodisilane in the hydrocarbon vehicle to favor formation for compound (A). If the hexachlorodisilane is added to the source of the diisopropylamino group, formation of compound (B) is favored. In the process of synthesizing the compound of formula (I) the metal aluminum hydride may be added to a mixture of the compound of formula (A) in the solvent, or vice versa. Reaction conditions may be readily optimized for different orders of addition in order to maximize the yield of and/or selectivity for synthesizing the compound of formula (I).

In some aspects the processes may be further defined as being any one of the species thereof described later in the working examples.

In some aspects the compound of formula (A) or (I) independently may be further defined by its isotopic composition. Each compound independently may be a natural abundance isotope form, alternatively an isotopically-enriched form, alternatively a mixture of said forms. The isotopically-enriched forms of the compound of formula (A) or (I) include forms that contain a greater-than-natural-abundance amount of deuterium, tritium, $^{29}Si$, $^{30}Si$, $^{32}Si$, or a combination of any two or more thereof. In addition to the uses of the compounds described herein, isotopically-enriched forms of the compounds may be useful in applications wherein detection of the isotopically-enriched compound or an isotopically-enriched silicon material (e.g., film) made therefrom would be helpful. Examples of such applications are medical research and anti-counterfeiting applications. Compounds of formula (A) or (I) having different isotopic compositions may differ from each other in at least one property, function, and/or use.

Each compound of formula (A) or (I) independently may be stored under an anhydrous condition (i.e., lacking water), under an inert atmosphere, or, typically, both, i.e., anhydrous inert atmosphere. The inert atmosphere may be a gas of molecular nitrogen, helium, argon, or a mixture of any two or more thereof. Compounds of formula (A) or (I) having different concentrations of water may differ from each other in at least one property, function, and/or use.

Any of the contacting steps independently may further comprise agitating the reactants. The agitating may enhance mixing and contacting together of the reactants and additional ingredients in the reaction mixture. Said contacting steps independently may use other conditions, with or without the agitating. The other conditions may be tailored to enhance the contacting, and thus reaction, of the reactants so as to form the intended reaction product in a particular contacting step. Said other conditions may be result-effective conditions for enhancing reaction yield or minimizing amount of a particular reaction by-product. Examples of said other conditions are atmosphere, temperature, and pressure. For example, the reduction and/or substitution contacting steps independently may be performed under an inert gas atmosphere such as a bleed of anhydrous argon or helium gas. Alternatively or additionally, the reduction and/or substitution contacting steps independently may comprise a temperature of the reactants of from a minimum temperature at which said reaction can be appreciated, up to the lower of the boiling point of the lowest boiling ingredient at a pressure employed. Reaction may be appreciated by detecting disappearance of reactants or appearance of product, e.g., by $^{29}$Si and/or $^1$H nuclear magnetic resonance (NMR) spectroscopy. For example, the contacting steps independently may comprise a temperature of the reactants of from −60° to 100° C., alternatively from −20° to 95° C., alternatively from 0° to 90° C., alternatively from 20° to 90° C. The contacting steps independently may be performed under less than ambient pressure, e.g., less than 101.3 kilopascals. The conditions used in the different ones of contacting steps may be the same as or different than the conditions used in any other contacting step(s) and/or the separating steps described herein.

In some aspects of the processes of synthesizing the compounds of formulas (A) and (I), if any one of the contacting steps is carried out for too long prior to initiating the separating step, the yield of the purified compounds of formulas (A) or (I), respectively, from the separating step may be undesirably decreased. Therefore, it may be advantageous to perform the contacting step and the separating step at the same time and under the same conditions. This co-performance of the contacting and separating steps may be done, for example, by contacting the reactants and vehicle (e.g., hydrocarbon vehicle or solvent, as the case may be) together under conditions useful for both performing the intended reaction and for separating the desired reaction product (e.g., the compound of formula (A) or (I) as the case may be) from the resulting reaction mixture such as via continuous distillation such as vacuum distillation. In this way the yields of the purified compounds of formulas (A) and (I) may be optimized under the conditions employed because as soon as it is made, the compounds are removed from the reaction mixtures, and optionally cooled.

In some aspects the process of synthesizing the compound of formula (I) uses as the source of the compound of formula (A), the reaction mixture directly as obtained from the contacting step of the process of synthesizing the compound of formula (A), and without purification. For example, the reaction mixture obtained from the process of synthesizing the compound of formula (A) may be stored until future use in the process of synthesizing the compound of formula (I). The storage may comprise cold storage at temperature ≤−50° C. Alternatively, as described earlier, the compound of formula (A) may be separated and/or purified from the reaction mixture containing same, and the resulting separated and/or purified compound of formula (A) may then be used in the process of synthesizing the compound of formula (I).

The separating step employed for separating the compounds of formulas (A) and (I) from their respective reaction mixtures synthesizing same may comprise any technique suitable for separating the compounds of formulas (A) or (I) from their respective reaction by-product product and any unreacted reactants or additional ingredients (e.g., vehicle). Different techniques may be preferred for different compounds of formulas (A) and (I). One technique may be employed or a sequence of two or more techniques may be employed. A given technique may be performed one time or repeated two or more times, each time with a product of a prior technique in order to iteratively decrease impurity content to yield an iteratively purified compound of formula (A) or (I), e.g., a purified compound of formula (A) having iteratively lower concentrations of alkylammonium chloride, or a purified compound of formula (I) having iteratively lower atomic concentrations of aluminum. Examples of suitable techniques are decanting, distilling, evaporating, extracting, filtering, freeze drying, gas chromatography, ion exchange chromatography, partitioning, phase separating, reverse phase liquid chromatography, stripping, volatilizing, and washing. Alternatively or additionally, each of the compounds of formulas (A) and (I) may be subjected to reverse phase liquid chromatography. Examples of suitable reverse phase liquid chromatography techniques are reverse phase medium pressure column chromatography (RP-MPLC) and reverse phase high pressure column chromatography (RP-HPLC), wherein the stationary phase is a solid such as silica gel and the mobile phase is an anhydrous, aprotic organic solvent such as anhydrous hexanes, anhydrous acetonitrile, anhydrous ethyl acetate, or a mixture of any two or more thereof.

For example, in some aspects of the processes of synthesizing the compounds of formulas (A) and (I), the contacting steps independently may produce a reaction mixture having therein a solid carried over into the contacting steps from an earlier step (from a optional preliminary step), and/or having therein a solid precipitate formed in situ therein as a solid reaction by-product during the syntheses. E.g., the solid reaction by-product may be $M^A X$ or $M^B X$ such as LiCl, NaCl, or the salts $M^A X_2$ or $M^B X_2$ such as $MgCl_2$ or $CaCl_2$, as the case may be depending on $M^A$ and $M^B$. In said aspects the separating step may comprise filtering such a reaction mixture to remove the solids such as salts to give a filtrate containing the compound of formula (A) or (I), as the case may be, and lacking solid reaction by-products.

After filtering off solid reaction by-products, the resulting filtrate, which contains the compound of formula (A) or (I), as the case may be, may be distilled or stripped to remove volatile components therefrom to give a remainder containing a concentrated form of the compound of formula (A) or (I), as the case may be. The volatile components removed in this way are components having a lower boiling point than the boiling point of the compound of formula (A) or (I), and may include, e.g., hydrocarbon vehicle, any unreacted diisopropylamine and/or pyridine or a trialkylamine, if any, and/or any reaction by-products of Si—Si bond cleavage such as diisopropylaminotrichlorosilane (all in the process of synthesizing the compound of formula (A)). The volatile component in the process of synthesizing the compound of formula (I) may be monosilane and/or any reaction by-products of Si—Si bond cleavage such as diisopropylaminosilane (i-Pr)$_2$NSiH$_3$.

Any reaction by-products and other ingredients of a reaction mixture having a lower boiling point than the boiling point of the compound of formula (A) or (I), as the case may be, may be removed therefrom via an evaporative method to give a remainder of a concentrated form of the compound of formula (A) or (I), respectively. The compound of formula (A) or (I) may be distilled or stripped from the remainder to give the purified compound of formula (A) or (I), as the case may be. The pot residue from the distillation or stripping may comprise another remainder containing any non-volatile reaction by-products and/or any non-volatile additional ingredients. The non-volatile components left behind in this way are components having a higher boiling point than the boiling point of the compound of formula (A) or (I) and may include, e.g., non-volatile vehicle such as the solvent or, in some aspects the second solvent, (e.g., in the process of synthesizing the compound of formula (I)) and/or oligomeric or polymeric by-products formed by condensation of two or more silane molecules during the contacting step.

The purity of the compounds of formula (A) and (I) independently may be determined by reverse phase liquid chromatography or, more likely, by gas chromatography (GC) as described later. For example, the aforementioned numerical values of purities of the compounds of formulas (A) and (I) may be area % (GC). Each ≤100 area % (GC) independently may be equal to 100 area % (GC), in which aspect the purified compound of formula (A) or (I) is the respective compound of formula (A) or (I) per se. Alternatively each 100 area % (GC) independently may be <100 area % (GC), in which aspect the purified compound of formula (A) or (I) is a composition containing at least one additional component other than the compound of formula (A) or (I). The maximum purity of the compound of formula (A) or (I) in the composition having <100 area % (GC) may be 99.9999999 area % (GC) ("nine 9's" purity), alternatively 99.999999 area % (GC) ("eight 9's" purity), alternatively 99.99999 area % (GC) ("seven 9's" purity), alternatively 99.9999 area % (GC) ("six 9's" purity), alternatively 99.999 area % (GC) ("five 9's" purity), alternatively 99.99 area % (GC) ("four 9's" purity), alternatively 99.9 area % (GC). It is believed that the compound of formula (I), or the composition that consists essentially of the foregoing six 9's to nine 9's purity of the compound of formula (I), may be particularly useful in making silicon materials for electronics and/or photovoltaic applications, wherein generally the higher the number of 9's purity the better the usefulness thereof in said applications.

Another inventive aspect is a process for reducing chloride levels in an aminosilane comprising combining i) a metal hydride or ii) a metal amide salt with an aminosilane composition comprising an aminosilane and a chloride species to produce a mixture of the aminosilane and a chlorine-containing reaction product formed by the reaction of the metal hydride or the metal amide salt and the chloride species; and separating the aminosilane from the reaction product.

The metal hydride and metal amide salt combined are as described above in the aspect for producing diisopropylaminodisilane.

The aminosilane in the aminosilane composition may be any aminosilane, alternatively the aminosilane is an aminodisilane, and alternatively the aminosilane is diisopropylaminodisilane as described above.

The aminosilane composition comprises a chloride species. The chloride species can be any compound comprising a chlorine atom bonded covalently or otherwise in the compound or free chlorine atoms from any source, alternatively the chloride species is a silane comprising a chlorine atom covalently bonded or is free chlorine atoms, alternatively the chloride species is an aminochlorosilane or aminochlorodisilane. Not wishing to be bound by theory, it is believed that when the chloride species is an aminochlorosilane or aminochlorodisilane, more, or new, aminosilane may be produced by the reaction of the metal hydride or the metal amide salt and aminochlorosilane and/or aminochlorodisilane.

The aminosilane composition comprises greater than 5 ppmw, alternatively greater than 10 ppmw, alternatively greater than 25 ppmw, alternatively greater than 100 ppmw, based on the weight of all materials in the aminosilane composition, of chloride.

The amount of chloride in the aminosilane composition can be determined by methods known in the art. For example, the amount of chloride can be determined by ion-chromatography.

The aminosilane produced in the mixture is as described above.

Not wishing to be bound by theory, it is believed that the chlorine-containing reaction product of the metal hydride or the metal amide salt and the chloride species may be a non-volatile material formed by the reaction with the chlorine atom of the chloride species. For example, the metal hydride or metal amide may react with aminochlorosilane impurities to form new aminosilane and another non-volatile chloride compound, the chlorine-containing reaction product. Further, it is believed that the metal hydride or metal amide salt may react with the chloride species, but not necessarily with the chlorine of the chloride species, to form a new material with a higher boiling point than the aminosilane. The aminosilane can then be separated from the higher boiling, non-volatile chlorine-containing reaction product easily through separation processes such as distillation.

In one embodiment, the mixture is distilled to separate the aminosilane from the chlorine-containing reaction product of the metal hydride or the metal amide salt and the chloride species.

The aminosilane separated by, for example, distillation comprises less than 20 ppmw, alternatively less than 10 ppmw, alternatively less than 5 ppmw, based on the weight of the aminosilane separated, of chloride.

Another inventive aspect is a process for synthesizing diisopropylamino-disilane, which is of formula (I): $[(CH_3)_2CH]_2NSiH_2SiH_3$ (I), the process comprising:

contacting a metal aluminum hydride with diisopropylamino-pentachlorodisilane to form diisopropylamino-disilane characterizable by a boiling point, wherein the metal of the metal aluminum hydride is an element of Group I or Group II of the Periodic Table of the Elements, wherein the contacting is under vacuum and at a temperature to vaporize the diisopropylamino-disilane after it is formed; and separating the diisopropylamino-disilane after it is formed from unreacted diisopropylamino-pentachlorodisilane and the metal aluminum hydride by distillation, wherein the distillation is conducted concurrently with the formation of the diisopropylamino-disilane.

The metal aluminum hydride, the diisopropylamino-pentachlorodisilane, and the diisopropylamino-disilane characterizable by a boiling point are as described above.

One skilled in the art would know how to conduct a basic distillation. However, the distillation in this aspect of the invention is conducted concurrently with the formation of the diisopropylamino-disilane. To conduct the distillation concurrently means that the distillation is begun as the diisopropylamino-disilane is formed. It is believed that by beginning the distillation as the diisopropylamino-disilane is formed will increase the yield because it will limit the time that the diisopropylamino-disilane is exposed to the metal aluminum hydride and result is less cleavage of the Si—Si disilane bond.

The contacting is at a temperature of at least 90° C., alternatively at least 80° C., alternatively at least 70° C.

The contacting is at a vacuum of from 1 to 100 torr, alternatively from 1 to 50 torr, alternatively from 10 to 25 torr.

Embodiments of the invention also include the following numbered aspects.

Aspect 1. A process of synthesizing diisopropylamino-pentachlorodisilane, which is of formula (A): $[(CH_3)_2CH]_2NSiCl_2SiCl_3$ (A), the process comprising: contacting, in a hydrocarbon vehicle, hexachlorodisilane ($SiCl_3SiCl_3$) with a source of diisopropylamino group to give a higher yield of the compound of formula (A) compared to the yield, if any, of a compound of formula (B): $[(CH_3)_2CH]_2NSiCl_2SiCl_2N[CH(CH_3)_2]_2$ (B), wherein i-Pr is isopropyl; wherein the source of diisopropylamino group is, relative to the hexachlorodisilane, from 0.50 to 1.19 molar equivalents of a metal diisopropylamide, $[(i-Pr)_2N]_m M^A$, alternatively a mixture of the metal diisopropylamide and diisopropylamine, wherein subscript m is 1 or 2, wherein when m is 1, $M^A$ is an element of Group I of the Periodic Table of the Elements and when m is 2, $M^A$ is an element of Group II of the Periodic Table of the Elements, or the source of diisopropylamino group is from 1.0 to 2.39 molar equivalents of diisopropylamine ($(i-Pr)_2NH$), alternatively of a mixture of the metal diisopropylamide and diisopropylamine, or the source of diisopropylamino group is a mixture of from 0.50 to 1.19 molar equivalents of diisopropylamine ($(i-Pr)_2NH$), alternatively a mixture of the metal diisopropylamide and diisopropylamine, and from 0.50 to 1.19 molar equivalents of pyridine or a trialkylamine ($Alkyl_3N$), wherein each alkyl independently a ($C_2$-$C_{10}$)alkyl.

Aspect 2. The process of aspect 1 wherein the metal diisopropylamide is used as the source of the diisopropylamino group in the contacting step and m is 1 and $M^A$ is lithium, sodium, or potassium; or m is 2 and $M^A$ is magnesium or calcium; and wherein the yield of the compound of formula (A) is greater than or equal to 30%.

Aspect 3. The process of aspect 1 or 2 wherein the metal diisopropylamide is used as the source of the diisopropylamino group in the contacting step and the molar equivalent of the metal diisopropylamide is from 0.9 to 1.1 relative to the hexachlorodisilane.

Aspect 4. The process of aspect 1 wherein the from 1.0 to 2.39 molar equivalents of diisopropylamine ($(i-Pr)_2NH$) is used as the source of the diisopropylamino group in the contacting step and the yield of the compound of formula (A) is greater than or equal to 30%.

Aspect 5. The process of aspect 1 wherein the mixture of the diisopropylamine and pyridine or a trialkylamine is used as the source of the diisopropylamino group in the contacting step and the molar equivalents of the diisopropylamine is from 0.9 to 1.1 and the molar equivalents of the pyridine or a trialkylamine is from 0.9 to 1.1, both relative to the hexachlorodisilane, and wherein the yield of the compound of formula (A) is greater than or equal to 30%.

Aspect 5.01. The process of aspect 1, wherein the contacting, in the hydrocarbon vehicle, of the hexachlorodisilane ($SiCl_3SiCl_3$) with the source of diisopropylamino group is by adding the source of the diisopropylamino group to the hexachlorodisilane.

Aspect 6. The process of any one of aspects 2-5 wherein the process produces a reaction by-product that is a solid and the process further comprises separating the diisopropylamino-pentachlorodisilane from the solid reaction by-product to give a solution comprising the diisopropylamino-pentachlorodisilane in the hydrocarbon vehicle, the solution being free of the solid reaction by-product.

Aspect 7. The process of any one of the preceding aspects further comprising step (a) or (b): (a) separating the hydrocarbon vehicle from the diisopropylamino-pentachlorodisilane to give a concentrated form of the diisopropylamino-pentachlorodisilane; or (b) further comprising separating the hydrocarbon vehicle from the diisopropylamino-pentachlorodisilane to give a concentrated form of the diisopropylamino-pentachlorodisilane and distilling the diisopropylamino-pentachlorodisilane from the concentrated form thereof to give a purified form of the diisopropylamino-pentachlorodisilane in at least 50% yield and a purity greater than or equal to 90 area % (GC).

Aspect 8. A process of synthesizing diisopropylamino-disilane, which is of formula (I): $[(CH_3)_2CH]_2NSiH_2SiH_3$ (I), the process comprising: Contacting, in a solvent characterizable by a boiling point, a metal aluminum hydride with diisopropylamino-pentachlorodisilane to give diisopropylamino-disilane characterizable by a boiling point, wherein the metal of the metal aluminum hydride is an element of Group I or Group II of the Periodic Table of the Elements and the boiling point of the solvent is at least 90° C. and is at least 10 degrees Celsius higher than the boiling point of diisopropylamino-disilane; and Separating the diisopropylamino-disilane from the solvent to give a purified form of the diisopropylamino-disilane in at least 30% yield and a purity greater than or equal to 70 area % (GC).

Aspect 9. The process of aspect 8 wherein the solvent is an alkylene glycol dialkyl ether and the alkylene glycol dialkyl ether is a tetraethylene glycol di($C_1$-$C_4$)alkyl ether, propylene glycol di($C_4$-$C_8$)alkyl ether, ethylene glycol di($C_4$ or $C_8$)alkyl ether, or a combination of any two or more thereof.

Aspect 10. The process of aspect 9 wherein the alkylene glycol dialkyl ether is tetraethylene glycol dimethyl ether, propylene glycol dioctyl ether, or ethylene glycol dioctyl ether.

Aspect 11. The process of any one of aspects 8-10 wherein the boiling point of the solvent is at least 50° C. higher than the boiling point of diisopropylamino-disilane.

Aspect 12. The process of aspect 8 wherein the process comprises: Contacting, in a solvent characterizable by a boiling point, a metal aluminum hydride with bis(diisopropylamino)-pentachlorodisilane to give diisopropylamino-disilane characterizable by a boiling point that is at least 10° C. higher than the boiling point of the solvent; adding a second solvent characterizable by a boiling point that is at least 10° C. higher than the boiling point of the diisopropylamino-disilane; separating the solvent from the diisopropylamino-disilane and the second solvent; and then separating the diisopropylamino-disilane from the second solvent to give a purified form of the diisopropylamino-disilane in at least 30% yield and purity of at least 70 area % (GC).

Aspect 13. The process of any one of aspects 8-12 wherein the contacting is performed at a temperature of from −60 degrees Celsius (° C.) to 100° C. provided that the temperature is greater than the freezing point of the reaction mixture formed in the contacting step; and the contacting is continued for a period of time sufficient to give the diisopropylamino-disilane in greater than 30% yield.

Aspect 14. A process of synthesizing diisopropylamino-disilane, which is of formula (I): $[(CH_3)_2CH]_2NSiH_2SiH_3$ (I), the process comprising parts A and B: Part A: Contacting, in a hydrocarbon vehicle, hexachlorodisilane ($SiCl_3SiCl_3$) with, relative to the hexachlorodisilane, from 0.50 to 1.19 molar equivalents of a metal diisopropylamide, $[(i-Pr)_2N]_m M^A$, wherein subscript m is 1 or 2, wherein when m is 1, $M^A$ is an element of Group I of the Periodic Table of the Elements and when m is 2, $M^4$ is an element of Group II of the Periodic Table of the Elements, or with from 1.0 to 2.39 molar equivalents of diisopropylamine, or with a mixture of from 0.50 to 1.19 molar equivalents of diisopropylamine ((i-Pr)$_2$NH) and from 0.50 to 1.19 molar equivalents of triethylamine (Et$_3$N), to give a higher yield of diisopropylamino-pentachlorodisilane compared to the yield, if any, of a compound of formula (B): [(CH$_3$)$_2$CH]$_2$NSiCl$_2$SiCl$_2$N[CH(CH$_3$)$_2$]$_2$ (B), wherein i-Pr is isopropyl and Et is ethyl; and Part B: Contacting, in an alkylene glycol dialkyl ether characterizable by a boiling point, lithium aluminum hydride (LiAlH$_4$) with the diisopropylamino-pentachlorodisilane from Part A to give diisopropylamino-disilane characterizable by a boiling point, wherein the boiling point of the alkylene glycol dialkyl ether is at least 30 degrees Celsius higher than the boiling point of diisopropylamino-disilane; and Separating the diisopropylamino-disilane from the alkylene glycol dialkyl ether to give a purified form of the diisopropylamino-disilane in at least 30% yield for Part B and a purity greater than or equal to 70 area % (GC).

Aspect 15. The process of aspect 14, wherein Part A is performed according to the process of any one of aspects 2-7; Part B is performed according to the process of any one of aspects 9-13; or both.

Aspect 16. A composition comprising the compound synthesized by the process of any one of the preceding aspects and at least one reaction by-product of that process.

Aspect 17. The process of any one of aspects 1, 5, and 15, wherein the pyridine or a trialkylamine is the trialkylamine, and the trialkylamine is triethylamine, tripropylamine, or tributylamine.

The invention is further illustrated by, and an invention embodiment may include any combinations of features and limitations of, the non-limiting examples thereof that follow.

GC-FID conditions: a capillary column with 30 meters length, 0.32 mm inner diameter, and containing a 0.25 μm thick stationary phase in the form of a coating on the inner surface of the capillary column, wherein the stationary phase was composed of phenyl methyl siloxane. Carrier gas was helium gas used at a flow rate of 105 mm per minute. GC instrument was an Agilent model 7890A gas chromatograph. Inlet temperature was 150° C. GC experiment temperature profile consisted of soaking (holding) at 50° C. for 2 minutes, ramping temperature up at a rate of 15° C./minute to 250° C., and then soaking (holding) at 250° C. for 10 minutes.

GC-MS instrument and conditions: Sample was analyzed by electron impact ionization and chemical ionization gas chromatography-mass spectrometry (EI GC-MS and CI GC-MS). Agilent 6890 GC conditions included a DB-1 column with 30 meters (m)×0.25 millimeter (mm)×0.50 micrometer (μm) film configuration. An oven program of soaking at 50° C. for 2 minutes, ramping at 15° C./minute to 250° C., and soaking at 250° C. for 10 minutes. A helium carrier gas flowing at constant flow of at 1 mL/minute and a 50:1 split injection. Agilent 5973 MSD conditions included a MS scan range from 15 to 800·Daltons, an EI ionization and CI ionization using a custom CI gas mix of 5% NH$_3$ and 95% CH$_4$.

$^{29}$Si-NMR instrument and solvent: a Varian 400 MHz Mercury spectrometer was used. C$_6$D$_6$ was used as the solvent.

$^1$H-NMR instrument and solvent: a Varian 400 MHz Mercury spectrometer was used. C$_6$D$_6$ was used as the solvent.

IC instrument and sample Details: Samples were prepared by placing 0.2 to 0.3 g in an open 50 mL polypropylene centrifuge tube. The sample was then dissolved in 10 mL of toluene. The toluene solution was treated dropwise with 10 mL of deionized water (with periodic manual agitation to mix the toluene and water phases) in a fume hood. The loosely capped (to allow venting) sample mixture was allowed to stand approximately an hour in a hood. The sample was then capped and manually agitated for approximately one minute and then centrifuged. An aliquot of the bottom aqueous layer was filtered through a 0.45 micron nylon membrane syringe filter and analyzed by ion chromatography.

Anion analyses were performed on an ICS-5000 ion chromatograph equipped with a 0.4 mm×150 mm AS18-fast column, a 0.4 microliter sample loop and a conductivity detector. A KOH gradient was used for elution.

| | |
|---|---|
| −7.0 to 0.0 minutes | 5 mM KOH (equilibration) |
| 0-1 minutes | 5 mM KOH |
| 1-20 minutes | 5-20 mM KOH linear ramp |
| 20-30 minutes | 20 mM KOH |
| 30-31 minutes | 20-40 mM KOH |
| 31 minutes | stop run |

Flow=10 microliters/min, suppressor=ACES 300, current=7 mA. Stock solution used for anion IC standards was SPEX Certiprep ICMIX6-100, lot 21-36VYY.

Ambient temperature is about 23° C. unless indicated otherwise.

Example (Ex.) 1: synthesis of diisopropyl-pentachlorodisilane using 2.21 mol equiv. of diisopropylamine: mixed hexachlorodisilane (HCDS; 20.0 milliliters (mL), 0.116 mol) and anhydrous hexanes (200 mL) in a 1 liter (L) round-bottom flask. Cooled the mixture to −20° C. with dry ice. Under agitation of a mechanical stirrer, added a solution of diisopropylamine (DiPA; 35.8 mL, 0.256 mol) in hexanes (100 mL) in 35 minutes near −20° C. After the addition, warmed the slurry to 23° C., and stirred (bodied) for one night. Added another 100 mL hexanes to dilute the slurry, and filtered the diluted slurry through a Type D glass frit covered with 1 inch of thick diatomaceous earth (CELITE). Rinsed the resulting filtercake with 100 mL hexanes. Collected a clear filtrate (about 400 mL). Distilled the filtrate under vacuum (<1 Torr) to remove volatile organics. Recovered 28.43 g (73.5% yield) of crude diisopropyl-pentachlorodisilane as a clear yellowish liquid.

Ex. 2: synthesis of diisopropyl-pentachlorodisilane using 1.10 mol equiv. of diisopropylamine and 1.10 mol equiv. triethylamine: replicate the procedure of Ex. 1 except instead of the 35.8 mL of DiPA in hexanes (100 mL) use a solution of DiPA (17.9 mL, 0.128 mol) and triethylamine (17.8 mL, 0.128 mol) in hexanes (100 mL). The amount of clear filtrate was about 450 mL. After distillation to remove volatile organics, recovered 29.2 g (75.5% yield) of crude diisopropyl-pentachlorodisilane as a clear yellowish liquid.

Ex. 3: synthesis of diisopropyl-pentachlorodisilane using 1.10 mol equiv. of lithium diisopropylamide: mixed 10.0 M n-BuLi solution in hexanes (92.0 mL; 0.920 mol) and anhydrous hexanes (828 mL) in a 2 L round-bottom flask. Under agitation of a magnetic stirrer, added DiPA (129.0 mL, 0.920 mol) in 15 minutes at up to 40° C. Stirred the resultant lithium diisopropylamide solution for 1 hour at 23° C. To another 2 L round-bottom flask added HCDS (144.0 mL, 0.836 mol) and 93.1 mL hexanes. Cooled the 2$^{nd}$ flask with some dry ice near 0° C. Under agitation of a mechanical stirrer, pressure fed at a feed rate the lithium diisopropylamide solution through a ¼ inch (0.635 centimeter (cm)) inner diameter poly(tetrafluoroethylene) tubing into the $2^{nd}$ flask. A white precipitate formed immediately. Controlled the feed rate to maintain the reaction temperature below 40° C. The addition took 1 hour 15 minutes. After the addition, stirred (bodied) the slurry for one night. Then filtered the slurry and removed volatile organics using the procedures analogous to those as in Ex. 1 to give 199.8 g (71.6% yield) of crude diisopropyl-pentachlorodisilane as a clear yellow liquid.

Ex. 4: distilled diisopropyl-pentachlorodisilane from the crude diisopropyl-pentachlorodisilane of Ex. 1 to give a distillate comprising purified diisopropyl-pentachlorodisilane.

Ex. 5: synthesis of diisopropylamino-disilane: Added tetraethylene glycol dimethyl ether (TEGDME, 760 mL) to a 2 L round bottom flask. Cooled the TEGDME to 0° C. with dry ice, and then poured in powdery $LiAlH_4$ (63.5 g, 1.67 mol) under a nitrogen blanket in 15 minutes. Mechanically stirred the resultant slurry for 30 minutes at 0° to 6° C., and then deoxygenated the slurry under full vacuum (less than 1 Torr). Cooled the resultant slurry of $LiAlH_4$ to −20° C. with dry ice. Introduced a constant flow of nitrogen gas to sweep the headspace of the flask and vent through a bubbler into air at a moderate flow rate (2,000 mL/hour). Added into the flask the distilled diisopropyl-pentachlorodisilane (446.5 g, 1.34 mol) of Ex. 4 in 2.5 hours at less than −10° C. through an addition funnel. After the addition, warmed the reaction mixture to 23° C., and agitated for one night under the constant nitrogen sweeping. Then using a simple vacuum distillation apparatus under full vacuum (less than 1 Torr), heated the reaction mixture incrementally to 100° C., and collected 141.2 g crude diisopropylamino-disilane (DPDS, 65.4% yield) as a clear colorless liquid. The crude DPDS contained 85% (area) of DPDS as quantified with GC-FID. Fractionally distilled the crude DPDS to give purified DPDS having 98 area % (GC) purity.

Ex. 6: Several reagents were tested on a small (2-6 g) scale of low-chloride DPDS. After a set amount of time, the product was distilled through a 150 mm Vigreux column, weighed for yield, analyzed by $^1H$ NMR for composition, and submitted for ion chromatography (IC) analysis to determine the chloride concentration of the distilled product. The DPDS used was sourced from two batches of DPDS with different chloride concentrations (580 ppm Cl; and 78 ppm Cl). The results are in the following Table.

| Sample | $[Cl]_0$ (ppm) | $[Cl]_F$ (ppm) | Time (h) | Initial DPDS (g) | Final DPDS (g) | Quantity of Reagent | Product Decomp. |
|---|---|---|---|---|---|---|---|
| LDA | 580 | 54 | 0.5 | 3.01 | 1.68 | 0.01 g | No |
| LDA | 78 | 8 | 18 | 6.03 | 4.38 | 0.10 g | No |
| 0.5M LDA in TEGDME | 580 | 17 | 2 | 3.68 | 1.30 | 0.32 g | No |
| Superhydride | 580 | 2 | 2 | 2.45 | 1.33 | 1.2 mL | No |
| $NaB(H)Et_3$ | 580 | 211 | 0.5 | 3.18 | 1.24 | 0.5 mL | No |
| 0.18M $LiAl(H)(OtBu)_3$ in TEGME | 78 | 6 | 2 | 4.04 | 2.51 | 2.0 mL | Yes |

$[Cl]_0$ is starting chloride.
$[Cl]_F$ is final Chloride.
"Superhydride" is lithium triethylborohydride.
"LDA" means lithium diisopropyl amide.

Ex. 7: A batch of crude DPDS was prepared and contained chloride species as impurities. IC analysis of the crude DPDS revealed it to have a high chloride concentration of 2752 ppm (ca. 0.3%). All samples were stirred using a magnetic stir bar set to 300 rpm. A blank distillation of the crude DPDS lowered the chloride concentration to 1556±186 ppm. The vacuum used for this distillation was approximately $10^{-2}$ torr.

| Sample | $[Cl]_0$ (ppm) | $[Cl]_F$ (ppm) | Time (h) | Initial DPDS (g) | Final DPDS (g) | Max Pot (Mantle) Temp (° C.) | Quantity of Reagent |
|---|---|---|---|---|---|---|---|
| Blank | 2752 | 1556 ± 186 | NA | 10.00 | 8.34 | 63.0 (152) | NA |
| LDA Slurry in TEGDME | 2752 | 1142 | 3.1 | 10.01 | 8.22 | 84.6 (148) | 0.51 g |
| LDA Slurry in TEGDME | 2752 | 949 ± 6 | 3.2 | 10.01 | 8.00 | 82.3 (142) | 1.00 g |
| Superhydride | 2752 | 26 | 3.2 | 10.00 | 8.34 | 71.2 (172) | 2.0 mL |

$[Cl]_0$ is starting chloride.
$[Cl]_F$ is final Chloride.
"Superhydride" is lithium triethylborohydride.
"LDA" means lithium diisopropyl amide.
"TEGDME" means tetraethylene glycol dimethylether.

Ex. 8: 1.2 grams of Lithium Aluminum Hydride were loaded into 12 grams of tetraethylene glycol dimethyl ether in an agitated jacketed flask forming a slurry. Diisopropylaminochlorodisilane (7.5 grams) was loaded in a separate agitated jacketed flask. Both jacketed flasks were heated to 60° C. Vacuum (~28 inHg) was applied to the flask loaded with Diisopropylaminochlorodisilane. The heated slurry was slowly added to the chlorosilane. An exothermic reaction was observed with a temperature increase up to 90° C. Approximately 1 gram of material was collected overhead being condensed through a jacketed/coil condenser at 0° C. GC_TCD analysis was performed on the overhead material. The resulting mixture contained about 34% Diisopropylaminodisilane with the majority of the remaining composition being high boiling materials.

Ex. 9: The DPDS used in these experiments were prepared in situ using 3.69 g of LAH (lithium aluminum hydride) slurried in 51.0 g of TEGDME. The pot was set to cool to −15° C. and the addition of the diisoproylaminepentachlorodisilane (DPDC) to the LAH slurry was started when the pot reached −5° C. The 25 g of DPDC was added over about 20 minutes. After the DPDC addition was complete, the pot was sequentially warmed to 0, 10, and 20° C. at about 5 minute intervals and then stirred for 30 minutes at room temperature. The chloride removal agent was then added and the reaction mixture was stirred for 3 h prior to stripping. During the stripping process, the pot was sequentially heated to 50, 60, 70, 80, 90, 100, and 110° C. under full vacuum—the receiving flask was cooled to −20° C. Stripping took about 50 minutes for each sample. The results from these trials is in the following table.

| Sample | [Cl] (ppm) | Time (h) | Max Pot Temp (° C.) | Vacuum (torr) | DPDC (g) | DPDS (g) | Exotherm (° C.) | Quantity of Reagent |
|---|---|---|---|---|---|---|---|---|
| Superhydride | 33 | 3.5 | 108 | 7.0 | 25.0 | 3.7 | 3 | 4.0 mL |
| LDA Slurry in TEGDME | 253 ± 15 | 3.0 | 108 | 17.9 | 25.9 | 6.21 | 0 | 2.16 g |

LAH (10.94 g) was mixed with 156 g of TEGDME and cooled to −15° C. 74.7 g of DPDC was added to the pot over 47 minutes resulting in the pot temperature to warm to a maximum temperature of 11° C. due to the exothermic reaction. The pot was ramped to first 10° C. over 5 minutes and then 20° C. over 10 minutes. The mixture was stirred for 30 minutes. 8 mL of 1.5 M LDA/THF in cyclohexane was added to the mixture resulting a 2 degree exotherm. The pot was stirred for 3 h. The stripping occurred over 70 minutes with a maximum temperature of 110° C. and maximum vacuum of 2.3 torr. Each run generated about 22 g of product. This yielded crude DPDS samples with chloride concentrations of 310 and 286 ppm of chloride, respectively.

The fractions were combined to give 44.7 g of crude DPDS which were combined and then fractionally distilled. The pot was initially warmed to 50° C. whereas the condenser and receiver were cooled to −25° C. and pressure was reduced to 30 torr. The heating fluid temperature was raised to 60° C. while pressure was reduced to 22 torr which caused the crude mixture to reflux. The forecut came over when the pot temperature read 57° C. and the pressure read 19 torr. 8 grams of material was collected. The product cut was collected when the pot temperature read 78° C. and a pressure of 19.7 torr. 13 g of product was collected. The remaining 23.7 g of material was claimed as the pot. The chloride concentration for each fraction are as follows: forecut-40 ppm, product cut-54 ppm, and heel-727 ppm.

The below claims are incorporated by reference here, and the terms "claim" and "claims" are replaced by the term "aspect" or "aspects," respectively. Embodiments of the invention also include these resulting numbered aspects.

What is claimed is:

1. A process of synthesizing diisopropylamino-disilane, which is of formula (I): $[(CH_3)_2CH]_2NSiH_2SiH_3$ (I), the process comprising:
    contacting in a solvent, a metal aluminum hydride with diisopropylamino-pentachlorodisilane, to give diisopropylamino-disilane, wherein the metal of the metal aluminum hydride is an element of Group I or Group II of the Periodic Table of the Elements; and
    separating the diisopropylamino-disilane from the solvent and an optional second solvent to give a purified form of the diisopropylamino-disilane, wherein the solvent or the optional second solvent has a boiling point of at least 90° C. and at least 10° C. higher than the boiling point of diisopropylamino-disilane, and wherein the optional second solvent is combined with the solvent before, after, or during the contacting and prior to the separating.

2. The process of claim 1 comprising one of the following limitations e) or f):
    e) wherein the solvent or the optional second solvent is an alkylene glycol dialkyl ether and the alkylene glycol dialkyl ether is a tetraethylene glycol di($C_1$-$C_4$)alkyl ether, propylene glycol di($C_4$-$C_8$)alkyl ether, ethylene glycol di($C_4$ or $C_8$)alkyl ether, or a combination of any two or more thereof
    f) wherein the solvent is characterizable by a boiling point that is at least 10° C. less than the boiling point of the diisopropylamino-disilane; the second solvent is present and is characterizable by a boiling point that is at least 10° C. higher than the boiling point of the diisopropylamino-disilane; the solvent is first separated from the diisopropylamino-disilane and the second solvent and then the diisopropylamino-disilane is separated from the second solvent to give a purified form of the diisopropylamino-disilane in at least 30% yield and purity of at least 70 area % (GC).

3. A process of synthesizing diisopropylamino-disilane, which is of formula (I):

$[(CH_3)_2CH]_2NSiH_2SiH_3$ (I), the process comprising parts A and B:

Part A:
contacting, in a hydrocarbon vehicle, hexachlorodisilane ($SiCl_3SiCl_3$) with, relative to the hexachlorodisilane, from 0.50 to 1.19 molar equivalents of a metal diisopropylamide, $[(i-Pr)_2N]_m M^A$, wherein subscript m is 1 or 2, wherein when m is 1, $M^A$ is an element of Group I of the Periodic Table of the Elements and when m is 2, $M^A$ is an element of Group II of the Periodic Table of the Elements, or with from 1.0 to 2.39 molar equivalents of diisopropylamine, or with a mixture of from 0.50 to 1.19 molar equivalents of diisopropylamine ($(i-Pr)_2NH$) and from 0.50 to 1.19 molar equivalents of triethylamine (Et₃N), to give a higher yield of diisopropylamino-pentachlorodisilane compared to the yield, if any, of a compound of formula (B): [(CH₃)₂CH]₂NSiCl₂SiCl₂N[CH(CH₃)₂]₂ (B), wherein i-Pr is isopropyl and Et is ethyl; and Part B:

Contacting, in an alkylene glycol dialkyl ether characterizable by a boiling point, lithium aluminum hydride (LiAlH₄) with the diisopropylamino-pentachlorodisilane from Part A to give diisopropylamino-disilane characterizable by a boiling point, wherein the boiling point of the alkylene glycol dialkyl ether is at least 30 degrees Celsius higher than the boiling point of diisopropylamino-disilane; and Separating the diisopropylamino-disilane from the alkylene glycol dialkyl ether to give a purified form of the diisopropylamino-disilane in at least 30% yield for Part B and a purity greater than or equal to 70 area % (GC).

4. The process of claim 1 further comprising combining i) a metal hydride or ii) a metal amide salt with the diisopropylaminodisilane either before or after the separating.

5. The process of claim 4, wherein the metal hydride is lithium tris-(tert-butoxy)-aluminum hydride, lithium triethylborohydride, or sodium triethylborohydride and the metal amide is lithium diisopropylamide.

6. A process of synthesizing diisopropylamino-disilane according to claim 1, wherein the contacting is under vacuum and at a temperature to vaporize the diisopropylamino-disilane after it is formed; and separating the diisopropylamino-disilane after it is formed from unreacted diisopropylamino-pentachlorodisilane and the metal aluminum hydride by distillation, wherein the distillation is conducted concurrently with the formation of the diisopropylamino-disilane.

7. The process of claim 6, wherein the contacting is at a temperature of at least 90° C.

* * * * *